United States Patent [19]

Gorog et al.

[11] Patent Number: 5,296,379
[45] Date of Patent: Mar. 22, 1994

[54] APPARATUS AND METHOD FOR MODELING ARTERIAL THROMBUS FORMATIONS

[76] Inventors: Peter Gorog; Iren Kovacs, both of 20 Grenville Court, Lymer Avenue, London, United Kingdom, SE1G 1LR

[21] Appl. No.: 927,284

[22] PCT Filed: Mar. 22, 1991

[86] PCT No.: PCT/GB91/00438
§ 371 Date: Sep. 22, 1992
§ 102(e) Date: Sep. 22, 1992

[87] PCT Pub. No.: WO91/14943
PCT Pub. Date: Oct. 3, 1991

[30] Foreign Application Priority Data

Mar. 23, 1990 [GB] United Kingdom .............. 9006520.2

[51] Int. Cl.⁵ ............................................. G01N 33/86
[52] U.S. Cl. ........................................ 436/69; 436/70; 422/73; 422/82.13; 73/64.41; 128/638
[58] Field of Search ...................... 436/69, 70; 422/73, 422/82.13, 100, 68.1; 128/638, 672; 73/64.41

[56] References Cited

U.S. PATENT DOCUMENTS

| | | | |
|---|---|---|---|
| 4,581,920 | 4/1986 | Völkl et al. | 73/64.41 |
| 4,780,418 | 10/1988 | Kratzer | 422/73 X |
| 4,797,369 | 1/1989 | Mintz | 422/73 X |
| 4,879,432 | 11/1989 | Vieillard | 422/73 X |
| 5,039,617 | 8/1991 | McDonald et al. | 422/73 X |
| 5,047,211 | 9/1991 | Sloane, Jr. et al. | 422/73 |
| 5,051,239 | 9/1991 | von der Goltz | 422/73 |
| 5,089,422 | 2/1992 | Brubaker | 422/73 X |

FOREIGN PATENT DOCUMENTS 0129425 12/1984 European Pat. Off. .
88102116 3/1988 World Int. Prop. O. .

*Primary Examiner*—James C. Housel
*Assistant Examiner*—Maureen M. Wallenhorst
*Attorney, Agent, or Firm*—Pollock, Vande Sande & Priddy

[57] ABSTRACT

Apparatus and method for modeling of thrombogenesis using haemostasis measuring devices. A sleeve member is provided on a blood-carrying tube to simulate an environment of a human artery. When punctured with a small needle, bleeding is simulated, permitting blood to be trapped between the sleeve and blood-carrying tube. The trapped blood communicates with the blood flowing in the tube, resulting in thrombus formation.

8 Claims, 2 Drawing Sheets

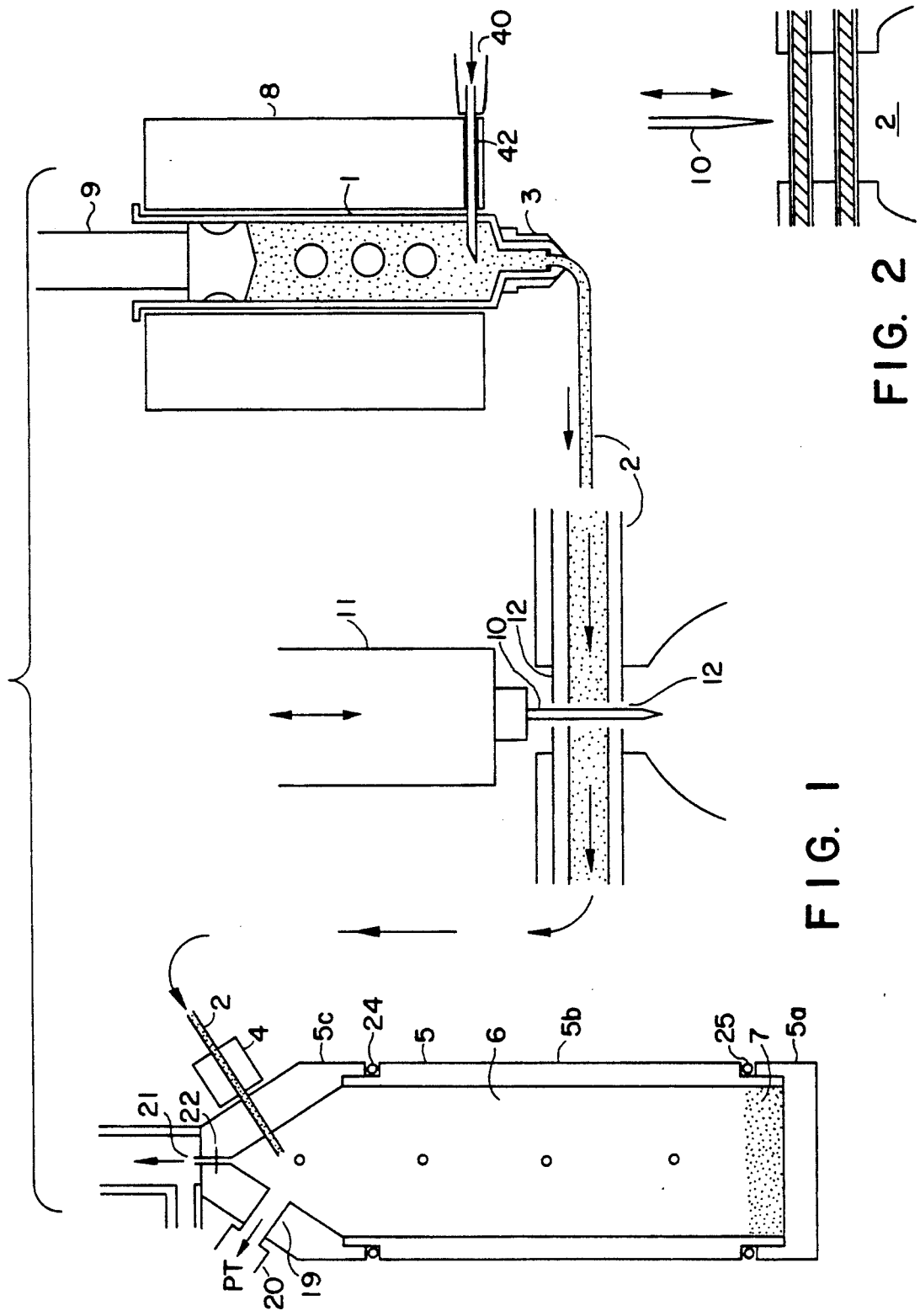

APPARATUS AND METHOD FOR MODELING ARTERIAL THROMBUS FORMATIONS

The present invention relates to the simulation and monitoring of arterial thrombus formations. Specifically, a method of modeling thrombus formations using haemostasis measuring devices is disclosed.

Arterial thrombosis is essentially a platelet plug formation on a damaged vessel wall. Normally, the lumen of the vessel wall is lined by a non-thrombogenic layer. When the deeper layers of the vessel wall are exposed to the flowing blood through damage, it is mainly collagen fibers embedded into the connective tissue which activates platelets and set in motion a chain of events leading to a sudden thrombus formation. The collagen-platelet interaction is therefore the major contributor to thrombogenesis.

Measurements of the physical attributes of blood in vitro has been described in previous patents and patent applications of the inventor. In PCT/GB87/00633, there is described a dual channel device for measuring various haemostasis clotting and the like properties of blood, and specifically to apparatus enabling measurements of such quantities to be made on blood. In the device described in the aforesaid published patent application, there is described a technique which permits the simulation of flowing blood through an artery, and the consequences of a sudden puncture to the tube carrying the flowing blood, thus simulating bleeding.

Described in the aforesaid published patent is a technique which permits the analysis of platelet plug-formation when a piece of collagen material is introduced into the flowing bloodstream. The collagen interacts with the flowing blood to activate platelets which result in thrombus formation on the surface of the collagen. The progress of thrombus formation is monitored by observing the blood flow in the tube, as indicated by the pressure at the distal end of the tube discharging the stream of blood. The formation of the thrombus on the collagen material eventually produces a pressure pattern which is indicative of the occlusion of the tube, thus modeling an arterial thrombogenesis occurring in a human blood vessel.

The present invention is a continuation of these efforts to measure the thrombus formation using the apparatus and techniques described in the earlier-published patent application.

SUMMARY OF THE INVENTION

It is therefore an object of this invention to accurately model arterial thrombus formation in vitro.

It is a more specific object of this invention to permit modeling of thrombogenesis which takes into account other factors contributing to the formation of a thrombus.

It is yet another object of this invention to provide an improved method for preparing collagen material for introduction in a flowing bloodstream to measure platelet formation.

These and other objects of the invention are accomplished with apparatus and methods using the haemostasis measuring techniques developed by the present inventor. Specifically, the haemostasis measuring devices and techniques of the foregoing prior patent applications of the inventor are further modified to study other subsidiary effects contributing to thrombogenesis.

In carrying out the invention, a simulation is made of an artery which is adjacent other human tissue, such that bleeding of the artery communicates with the tissue, which in turn, increases platelet plug-formation. The blood-carrying tube of the haemostasis measuring device is further provided with a sleeve surrounding the blood-carrying tube, which is punched during a haemostasis measuring session. Bleeding occurs through the blood-carrying tube into the sleeve member, also punched with a small bleeding hole. As the blood collects between the sleeve and blood-carrying tube, a certain portion of the collected blood communicates with the interior of the blood-carrying tube, generating a thrombus, as is found in blood vessel fissure and rupture.

Using the haemostasis measuring device, it is possible to measure the growth rate and volume of the thrombus by monitoring the pressure of the blood tube downstream from the thrombus.

As a further development, a technique has been discovered for preparing collagen material for introduction to a tube for measuring the effects of collagen material on platelet formation.

DESCRIPTION OF THE FIGURES

FIG. 1 illustrates the haemostasis measuring device described of the prior patent application.

FIG. 2 is an enlarged view of the punching needle and a pair of blood supply tubes positioned for simultaneous puncture by needle 10.

DESCRIPTION OF THE PREFERRED EMBODIMENT

Figure 3:
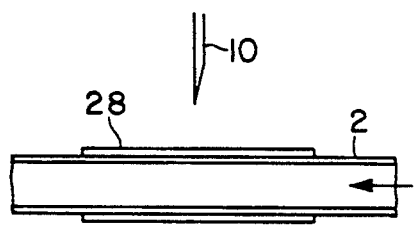
FIG. 3 illustrates the provision of a sleeve 28 over blood-carrying tube 2.

Referring now to FIG. 1, there is shown one channel from a dual, identical channel instrument for measuring haemostasis. The instrument includes a columnar container in the form of a 2 ml hypodermic syringe 1 for holding blood. An elongated polyethylene tube having an internal diameter of ½ mm and a length of 30 cm is connected to the syringe 1 by means of a Luer type connector 3, familiar to those skilled in the art. The tube 2 is inserted through a pressure-tight rubber seal 4 at the opposite end thereof to a waste blood holding vessel 5. Prior to measuring the properties of a blood sample using the device, the waste holding vessel 5 is filled with paraffin oil 6 and the level of blood 7 in the vessel rises during the investigation.

The syringe 1 is received in the syringe mounting block 8, having an electrical heating element and thermostat associated therewith, to maintain the blood sample at a constant temperature of 37° C. The plunger 9 of the syringe is secured by a lock, not shown, to prevent its backward movement upon pressurization of blood in the syringe.

The polyethylene tube 2 is threaded through a punching station, generally of the kind described in Published European Patent Specification No. 129425, except for the modification of the tube support to provide the punching of more than one polyethylene tube. A punching needle 10 is provided on the punch plunger 11, having sufficient shank length to pierce two parallel disposed blood tubes 2. FIG. 2 illustrates in detail how the two tubes are positioned with respect to each other to permit the simultaneous punching of both tubes. Punching needle 10 is configured to have a diameter of substantially 0.15 mm in order to provide a controlled bleeding from t respective polyethylene tubes 2.

The waste blood holding vessel 5 has three parts, a base 5a, a central tubular part 5b, and an upper part 5c. The upper part 5c has an opening 19 to which is affixed a pressure transducer 20. An outlet 21 for paraffin oil is also provided in the upper part 5c. A valve 22 is provided for closing outlet 21 from the vessel 5.

Parts 5a, 5b and 5c of vessel 5 are assembled as a push fit, and are sealed by O-rings 24 and 25. In operation of the dual channel device, two blood samples are taken from the patient using a respective pair of syringes 1 for the two-channel device. The syringes are placed in the heating block 8 of the apparatus, and the lower lock connector is connected to the syringe outlet. Respective tubes 2 are then passed through the piercing station, and through rubber seals 4 or two waste holding vessels 5.

Each of the respective syringes 1 is then pierced through its side with a respective hypodermic needle 42 and 43 connected to a paraffin oil supply. Paraffin oil is pumped into the syringes 1 at a rate of approximately 0.1 ml per minute. The inflowing paraffin oil prevents of red cells in the blood and displaces the blood through the tubing 2. The pressure at the transducer 20 is observed until it is steady with a steady flow of blood entering vessel 5. Tubes of both channels are then simultaneously pierced with a single needle 10 and the pressure at transducer 20 is observed further. A confirmatory check of bleeding through holes 12 is carried out, noting the signal received at a silicone photodiode implemented to detect blood droplets. Bleeding from holes 12 causes the amount of light incident to a photodetector to be much reduced, so that the onset and cessation of bleeding can be noted and confirmed.

The foregoing instrument has been used in studies of bleeding and the effects of various coagulants on blood in treating various blood disorders. The foregoing apparatus is useful in simulating actual in vivo conditions, and provides clinical studies of the physical properties of blood when treated with various agents.

As an improvement to the foregoing system, it is possible to further increase the in vivo simulation by applying a sleeve over the tube, simulating the body tissue normally surrounding the arteries of a patient. The sleeve 28, shown in FIGS. 3 and 4, may be of a silicone rubber material, which, when punctured along with the blood-carrying tube 2, will permit blood to escape and be trapped between the sleeve 28 and blood-carrying tube 2. When an acute occlusion arterial thrombus formation occurs in a blood vessel, it generally occurs by either (1) severe narrowing (stenoses) of the vascular lumen; (2) rupture of an atherosclerotic plaque; and, (3) hemorrhage related intravascular thrombus. The most frequent mechanism of acute coronary occlusion is a combination of the above factors. It is precipitated by the rupture of plaque and the bleeding into the vessel will result in an occlusive thrombus formation.

The embodiments shown in FIGS. 3, 4, 5, 6 and 7 illustrate a laboratory technique for modeling the complex process of thrombus formation. The thrombus model permits a study of the pathomechanism and the evaluation of drugs which are used to treat thrombogenesis.

Figure 4:
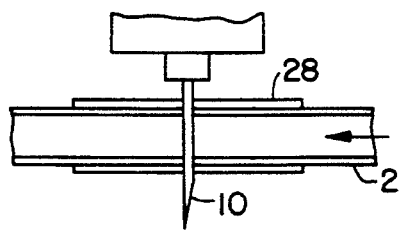
FIG. 4 illustrates the puncture of the sleeve and blood-carrying tube 2.
Figure 5:
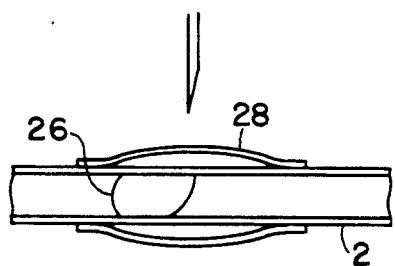
FIG. 5 illustrates the formation of a thrombus 26 within the blood tube 2.
Figure 6:
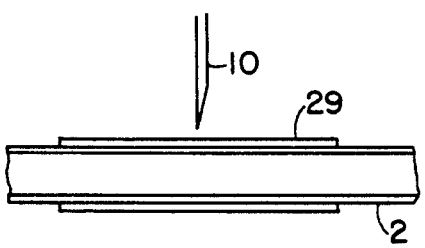
FIG. 6 illustrates the puncture of another type of sleeve material 29 which is an artery from an animal over a tube 2.
Figure 7:
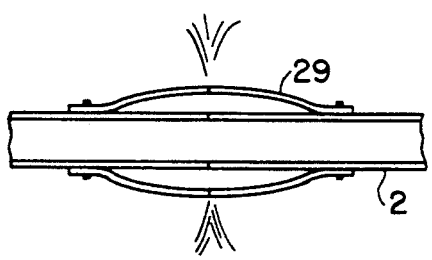
FIG. 7 illustrates the puncture of material 29 and tube 2 by the punching needle 10.

The polyethylene tubing 2 in FIGS. 3, 4 and 5 is surrounded by a silicone rubber sleeve at the punch site. By this arrangement, the needle penetrates both the outer rubber sleeve 28 and the polyethylene tubing. When the needle punches the sleeve 28 and tubing 2 of FIG. 4, the blood escapes from the interior of the elongate tube 2 into the space between the sleeve 28 and tube 2, and remains trapped between the tube 2 and sleeve 28. If the source 40 of paraffin oil is pulsed, such that pressure pulses are introduced in the blood flowing in tubes 2, occlusive thrombus 26 forms rapidly in the tube after punching. The thrombus 26 forms as a result of the blood flowing between the tube 2 and sleeve 28. Due to the pulsating nature of the bloodflow in an artery when an atherosclerotic ulcer ruptures, the possibility exists that communication occurs between the main blood flow and extravascular blood. This may, in turn, permit activating factors to reenter the artery lumen during the pulsating pressure wave occurring in the blood. The sleeve 28 simulates these effects, the sleeve 28 permitting blood exiting the tube puncture to reenter the bloodstream. This effect will result in thrombus formation 26 within the tubing 2 following the arrest of bleeding by haemostatic plugs formed in the punctured hole. The thrombus grows rapidly until approximately ⅔ of the lumen has been occluded when it is dislodged by the flowing blood.

Figure 8:
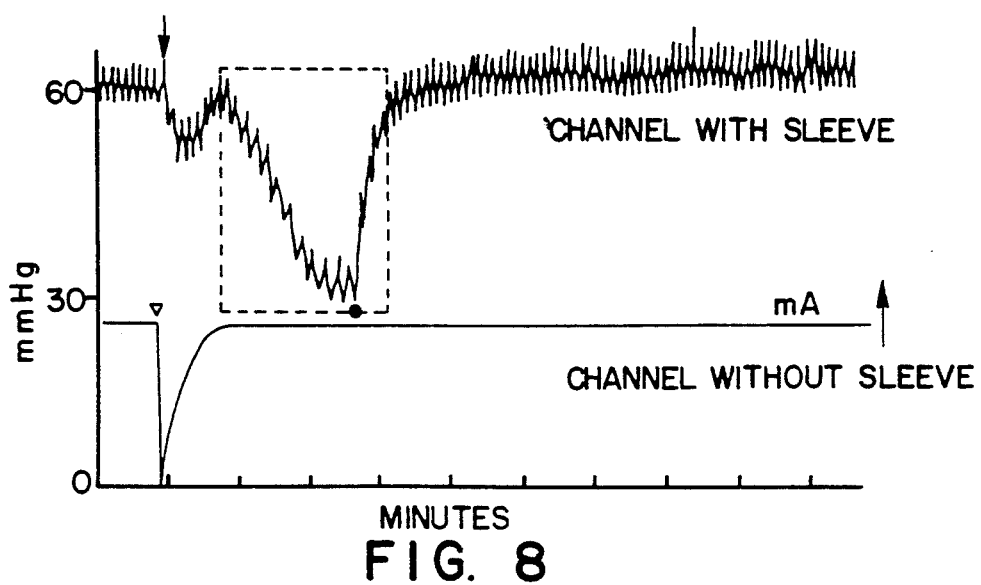
FIG. 8 illustrates the pressure reading by a pressure transduced (PT) downstream of the punching needle during the formation of a thrombus within blood-carrying tube 2 of FIGS. 3-5.

During this process, the downstream pressure measured by pressure transducer 20 provides the profile shown in FIG. 8. Referring further to this Figure, there can be seen the comparison of the channel bearing a sleeve 28 versus a channel having no sleeve 28. When the two channels are simultaneously punched, the measured downstream pressure immediately drops in both channels. In the channel having the sleeve member 28, shown as the upper trace of FIG. 8, the pressure will rise until bleeding occurs. This can be seen most clearly from the lower trace of FIG. 8 showing the downstream pressure profile of a channel not bearing the sleeve 28.

The region of the upper trace of FIG. 8, bounded by the dashed lines, illustrates the formation of a thrombus 26 within the sleeve 28. As the thrombus forms, the downstream pressure decreases as the tube is becoming occluded, reducing the flow rate of blood into the vessel 5. At a point shown at the lowermost point of the pressure profile, the pressure begins to rise again, indicating that the thrombus 26 has been dislodged, permitting the free flow of blood to occupy the entire diameter of the tube 2.

Thus, it is seen that the device with the improvements of FIGS. 3, 4, 5 and 6 permit an analysis of thrombus formation under the influence of any introduced agents to permit full experimentation to simulate or model occlusive thrombus formation.

As a variant of the foregoing technique, arterial vessel material 29 from an animal may be used in place of the silicone rubber sleeve 28. The use of animal blood vessel simulating the in vivo situation permits a full range of experimentation and conditions to be produced for examining occlusive thrombus formation.

In deriving the foregoing techniques for measuring thrombus formation, a method has been discovered for preparing surgical catgut suture for use in measuring platelet formation in accordance with the aforesaid patent. Commercially surgical catgut suture is normally provided in 75-150 cm lengths, rolled up and sealed in an alcohol solution. In preparing this collagen material for insertion in a blood-carrying tube of the haemostasis measuring device, catgut is permitted to dry at room temperature. The catgut is tensioned with a small weight, approximately 25 grams, and then moistened by a cotton wool pellet, soaked with distilled water. The wet catgut, suspended by the weight, is let dry at room temperature. The simple procedure results in a straight line of catgut having uniform and standard diameter. The catgut is then cut by a scalpel into segments and stored in a sealed tube. Immediately before testing in the haemostasis measuring device, one of these cut segments of catgut is placed in a Finn's forcep into the lumen of the polyethylene tubing, in which blood will be perfused. To prevent movement of the catgut in the blood tube during blood flow, a loop is formed from the polyethylene tubing housing the collagen fiber, downstream of the collagen fiber; the sharp curvature of the tubing does not impede the perfusion flow, but prevents the fiber from traveling along in the tubing when the resistance due to thrombus formation on collagen is increased.

Following this simple preparation technique permits accurate, reliable and repeatable data to be obtained to measure platelet thrombus-formation from different blood samples.

There has thus been demonstrated some improvements on the basic haemostasis technology for permitting the modeling of occlusive thrombus formation in the lumen of a blood vessel. Those skilled in the art will recognize yet other embodiments described more particularly by the claims which follow.

What is claimed is:

1. A method of modeling occlusive thrombosis formations in vitro comprising:

supplying blood from a pressurized blood reservoir to a tubing which passes through a punching station to a collection reservoir;

providing a sleeve over said tubing in a portion of the tubing which passes through said punching station;

punching a needle hole in said sleeve and tubing at said punching station to stimulate bleeding, whereby blood exits said tubing and a portion of said blood is trapped between said tubing and said sleeve, some of the trapped blood contacting blood in said tubing thus forming a thrombus in said tubing which increases in size with time, and subsequently moves past said punching station; and, measuring a change in pressure in said tube to identify the formation of the thrombus.

2. The method of claim 1 wherein said sleeve is a silicone rubber sleeve.

3. The method of claim 1 wherein said sleeve comprises a length of animal blood vessel surrounding said tubing, which is punched with said tubing, whereby the effect of said blood vessel material on the thrombus formation may be determined.

4. The method of claim 1 further comprising establishing a pulsamatile flow of blood in said tubing by pulsatile pumping a displacing medium into said pressurized blood reservoir.

5. An apparatus for modeling occlusion thrombosis in vitro comprising:

a reservoir of blood including an outlet, and a source of pressuring media for forcing blood through said outlet;

an elongate tube connected at one end to said outlet, having a portion which passes through a punching station and connected at an opposite end to a waste receptable;

a sleeve member disposed over the portion of said elongate tube which passes through a punching station positioned to be pierced by a needle of said punching station, whereby blood exits the tube and is trapped between an exterior wall of said elongate tube and an interior wall of said sleeve, said trapped blood contacting blood flowing through said elongate tube, thus inducing the formation of a thrombus in blood flowing in said elongate tube; and, a pressure gauge connected to said elongate tube to monitor the fluid pressure in said elongate tube downstream from said punching station.

6. The apparatus for modeling occlusion thrombosis in vitro of claim 5 further comprising mans for pulsing said source of pressurizing media to pulse blood flowing in said elongate tube.

7. The apparatus of claim 5 wherein said sleeve member is made from silicon rubber.

8. The apparatus of claim 5 wherein said sleeve member comprises a section of animal blood vessel disposed over said tube in the vicinity of said punching station.

* * * * *